(12) United States Patent  
Liphardt

(10) Patent No.: US 8,983,787 B1  
(45) Date of Patent: Mar. 17, 2015

(54) METHOD OF EVALUATING DATA QUALITY

(76) Inventor: Martin M. Liphardt, Lincoln, NE (US)

( * ) Notice: Subject to any disclaimer, the term of this patent is extended or adjusted under 35 U.S.C. 154(b) by 516 days.

(21) Appl. No.: 13/506,140

(22) Filed: Mar. 30, 2012

Related U.S. Application Data

(63) Continuation-in-part of application No. 12/653,299, filed on Dec. 11, 2009, now Pat. No. 8,600,703.

(60) Provisional application No. 61/201,473, filed on Dec. 12, 2008.

(51) Int. Cl.
*G01B 11/06* (2006.01)
*G01J 4/04* (2006.01)
*G01N 21/00* (2006.01)

(52) U.S. Cl.
USPC .................. 702/90; 356/369; 250/559.09

(58) Field of Classification Search
CPC ................................... G01B 11/0641
USPC .......................................... 702/90
See application file for complete search history.

(56) References Cited

U.S. PATENT DOCUMENTS

| | | | |
|---|---|---|---|
| 4,558,949 A | 1/1971 | Evans | 310/239 |
| 3,880,524 A | 4/1975 | Dill et al. | 356/369 |
| 4,006,293 A | 2/1977 | Bouwhuis et al. | 369/44.42 |
| 4,357,696 A | 11/1982 | Bierhoff et al. | 369/44.13 |
| 4,503,324 A | 3/1985 | Yokota | 250/201.5 |
| 4,531,162 A | 7/1985 | Tokumitsu | 386/76 |
| 4,589,773 A | 5/1986 | Ido et al. | 356/623 |
| 4,595,829 A | 6/1986 | Neumann et al. | 250/201.4 |
| 4,800,447 A | 1/1989 | Toba | 386/77 |
| 4,825,311 A | 4/1989 | Saito | 360/77.16 |
| 4,916,555 A | 4/1990 | Hathaway et al. | 386/78 |
| 4,935,827 A | 6/1990 | Oldershaw et al. | 360/77.16 |
| 5,003,406 A | 3/1991 | Hatanaka et al. | 386/77 |
| 5,136,149 A | 8/1992 | Fujiwara et al. | 250/201.5 |
| 5,187,617 A | 2/1993 | Kaminaga | 360/64 |
| 5,218,415 A | 6/1993 | Kawashima | 356/139.1 |
| 6,091,499 A | 7/2000 | Abraham et al. | 356/623 |
| 6,504,608 B2 | 1/2003 | Hallmeyer et al. | 356/369 |
| 6,633,831 B2 * | 10/2003 | Nikoonahad et al. | 702/155 |
| 6,734,967 B1 | 5/2004 | Piwonka-Corle et al. | 356/369 |
| 6,930,765 B2 | 8/2005 | Meeks et al. | 356/73 |
| 7,084,978 B1 | 8/2006 | Liphardt | 356/364 |
| 7,136,172 B1 * | 11/2006 | Johs et al. | 356/614 |
| 7,230,699 B1 | 6/2007 | Liphardt et al. | 356/364 |
| 7,304,737 B1 | 12/2007 | Liphardt et al. | 356/369 |
| 7,304,792 B1 | 12/2007 | Liphardt et al. | 359/385 |
| 2004/0117811 A1 | 6/2004 | Furuya et al. | |
| 2004/0179288 A1 | 9/2004 | Kagami et al. | |
| 2006/0055932 A1 * | 3/2006 | McCandless | 356/434 |
| 2008/0268486 A1 * | 10/2008 | Braig et al. | 435/14 |

* cited by examiner

Primary Examiner — Bryan Bui
(74) Attorney, Agent, or Firm — James D. Welch

(57) ABSTRACT

Methodology for determining uncertainty in a data set which characterizes a sample involving elimination of the influence of sample alteration drift caused by data set acquisition, and/or elimination of the influence of system drift during data acquisition.

8 Claims, 9 Drawing Sheets

METHOD OF EVALUATING DATA QUALITY

CROSS-REFERENCE TO EXISTING APPLICATIONS

This Application is a CIP of application Ser. No. 12/653,299 Filed Dec. 11, 2009 now U.S. Pat. No. 8,600,703, and therevia Claims Benefit of Provisional 61/201,473 Filed Dec. 12, 2008.

TECHNICAL FIELD

The present invention relates to data quality, and more particularly to methodology for determining uncertainty in a data set which characterizes a sample involving elimination of the influence of sample alteration drift caused by data set acquisition, and also elimination of the influence of system drift during data acquisition.

BACKGROUND

It is known in the areas of Ellipsometry, Polaralimetry and Reflectometry or the like, to acquire a data set, (eg. intensity, Ellipsometric PSI, Ellipsometric DELTA over Time), which characterizes a sample, by causing a beam of electromagnetic radiation to interact with the sample, and determining changes in the beam caused by said interaction.

It is also known that the act of observing a sample can cause change to occur thereto. For instance, especially over a prolonged time needed to make a plurality of measurements, energy delivered to a sample by a beam of electromagnetic radiation impinging thereupon can catalyze reaction of the sample surface with said atmospheric components to the end that deposition of said atmospheric components occurs onto said sample. This can lead to a measurable change, (ie sample drift), of, for instance, measured film thickness on said sample surface over time.

It is also known that data acquisition systems such as ellipsometers and reflectometers can change, (ie. systemic drift), during application thereof in monitoring a sample, leading to acquisition of data which falsely represents sample composition.

Known Patents which address handling data sets are:
U.S. Pat. No. 7,151,605 to Herzinger et al. describes a method of replacing data points in a data set determined to be bad, while maintaining the remainder of the data set; and
U.S. Pat. No. 7,307,724 to Liphardt et al. describes a method reducing the effect of noise in a data set.

Another known Patent, while not directly related to the handling of data sets is:
Patent to Johs et al., U.S. Pat. No. 6,034,777 which describes a method for compensating for the effects of the presence of polarization state affecting input/output, elements in an ellipsometer system.

Another reference identified is an EPO Application titled "Method and Apparatus for Measuring Thickness of Thin Films on Substrate", No. EP 1 577 636 B1 by Dianippon Screen Mfg., published Sep. 21, 2005.

Additional known Patents are:
Patent to Norton et al., U.S. Pat. No. 5,486,710;
Patent to Maris et al., U.S. Pat. No. 5,748,317;
Patent to Aspnes et al., U.S. Pat. No. 5,798,837 and further disclosed is a Published Application:
Published application by Meeks et al., No US2002/0015146.

Need exists for methodology that allows compensating for sample and/or systemic drift during data acquisition.

DISCLOSURE OF THE INVENTION

The present invention provides methodology for compensating a data set obtained over time, for drift in sample composition and/or drift in the operation of the data acquisition system that produces the data set.

In general, as noted, Data vs. Time can include change based on two sources, (Sample change and Measurement System change), which for two Sample points can be expressed:

DATA CHANGE1=SYSTEM DRIFT+SAMPLE DRIFT1; and

DATA CHANGE2=SYSTEM DRIFT+SAMPLE DRIFT2.

Further, a ratio of Sample Point Exposure Times T1 and T2 is: R12=T1/T2; and R21=T2/T1.

If said DATA CHANGE1 equation is subtracted from the DATA CHANGE2 equation the result is:

(SYSTEM DRIFT−SYSTEM DRIFT)+(SAMPLE DRIFT2−SAMPLE DRIFT1).

In the present invention it is assumed that the SAMPLE DRIFTS are proportional to the Times a Sample is subjected to an investigating electromagnetic beam, hence:

$$\frac{\text{SAMPLE DRIFT1}}{\text{SAMPLE DRIFT2}} = \frac{T1}{T2} = R12.$$

Likewise:

$$\frac{\text{SAMPLE DRIFT2}}{\text{SAMPLE DRIFT1}} = \frac{T2}{T1} = R21.$$

For emphasis, it is stated directly that in the present invention a change in a Sample based on exposure to an electromagnetic beam is presumed to be proportional to the time the Sample is exposure to the electromagnetic beam. For instance, if Sample Point 2 is exposed for a longer time than Sample Point 1, Point 2 will be affected to a greater extent, which is proportional to the ratio of exposure times.

Continuing, using the just above equations, and the assumed time of exposure proportionality to Sample Change, it can be written:

SAMPLE DRIFT1=R12(SAMPLE DRIFT2).

Thus:

(DATA CHANGE2−DATA CHANGE1)=SAMPLE DRIFT2−R12(SAMPLE DRIFT2)=SAMPLE DRIFT2(1−R12).

It is then a simple additional step to arrive at:

$$\text{SAMPLE DRIFT2} = \frac{(\text{DATA CHANGE2} - \text{DATA CHANGE1})}{(1 - R12)}.$$

A exactly similar derivation also provides:

$$\text{SAMPLE DRIFT1} = \frac{(\text{DATA CHANGE1} - \text{DATA CHANGE2})}{(1 - R21)};$$

which it is not believed necessary to show here.

It is also noted that the Data Changes 1 and 2 can be approximated as first order straight line fits to plotted acquired data, such as typically determined by least square error procedures. Other than linear dependencies are also possible, and the quality of the linear correction depends on the accuracy of this assumption. It is noted that for non-linear dependencies other equations, (eg. polynomial), can be derived.

With the above notation the Drift in data at Sample Point 2 can be expressed as:

$$\text{SAMPLE DRIFT2} = \frac{(\text{DATA CHANGE2} - \text{DATA CHANGE1})}{(1 - R12)};$$

and for Sample Point 1 as:

$$\text{SAMPLE DRIFT1} = \frac{(\text{DATA CHANGE1} - \text{DATA CHANGE2})}{(1 - R21)};$$

Further, additional relationships can be expresed as:

SYSTEM DRIFT=DATA CHANGE2−SAMPLE DRIFT2;

SAMPLE DRIFT1=DATA CHANGE1−SYSTEM DRIFT;

by simple algebraic manipulation of the original equations.

It should be readily appreciated that DATA CHANGE1 and DATA CHANGE2 can be measured, hence SAMPLE DRIFT1 AND SAMPLE DRIFT2 can be calculated from the first two equations just above. And from the later two equations just above SYSTEM DRIFT can, be obtained, knowing said calculated SAMPLE DRIFT1 or SAMPLE DRIFT2 and DATA CHANGE1 or DATA CHANGE2, respectively.

Continuing, in all following cases, the present invention methodology begins with:
 a) providing a system comprising:
 a source of a beam of electromagnetic radiation;
 a sample supporting stage;
 means for controlling where a beam of electromagnetic radiation from said source thereof impinges on a sample placed on said stage; and
 a detector of electromagnetic radiation which exits said sample.

CASE 1

In the case of the method of compensating a sample characterizing data set for sample drift, the methodology further comprises:
 b) causing said beam of electromagnetic radiation to impinge on a position on said sample so that it interacts therewith and enters said detector, so that said detector provides as output, a plurality of data points over time;
 said plurality of data points acquired in step b serving to identify sample drift if a plot thereof presents with an overall change.
Said method then further comprises:
 c) if the plurality of data points acquired from the position in step b present with an overall change, compensating said plurality of data points acquired in step b for the identified sample drift;
to the end that a sample characterizing data set which is compensated for sample drift is achieved.

CASE 2

In the case of compensating a sample characterizing data set for system drift during data acquisition, the methodology further comprises:
 b) causing a beam of electromagnetic radiation to impinge on a first position on said sample so that it interacts therewith and enters said detector, so that said detector provides as output, a first single data point in a brief period of time;
 c) causing said beam of electromagnetic radiation to impinge on a second position on said sample so that it interacts therewith and enters said detector, so that said detector provides as output, a plurality of data points over time;
 d) causing said beam of electromagnetic radiation to again impinge on said first position on said sample so that it interacts therewith and enters said detector, so that said detector provides as output, a second single data point in a brief period of time;
said first and second data points acquired from said first position on said sample in steps b and d serving to identify data acquisition system drift if they are different and a plot thereof presents with an overall change; and
said plurality of data points acquired in step c serving to identify sample drift if a plot thereof presents with an overall change.
Said method then further comprises:
 e) if the first and second data points acquired from said first position on said sample in steps b and d are different, compensating said plurality of data points acquired from the second position in step c for the identified system drift during data acquisition;
to the end that a sample characterizing data set which is compensated for data acquisition system drift during data acquisition is achieved.

CASE 3

In the case of the method of compensating a sample characterizing data set for sample and system drift during data acquisition, the methodology further comprises:
 b) causing a beam of electromagnetic radiation to impinge on a first position on said sample so that it interacts therewith and enters said detector, so that said detector provides as output, a first single data point in a brief period of time;
 c) causing said beam of electromagnetic radiation to impinge on a second position on said sample so that it interacts therewith and enters said detector, so that said detector provides as output, a plurality of data points over time;
 d) causing a beam of electromagnetic radiation to again impinge on said first position on said sample so that it interacts therewith and enters said detector, so that said detector provides as output, a second single data point in a brief period of time;
said first and second data points acquired from said first position on said sample in steps b and d serving to identify data acquisition system drift if they are different and a plot thereof presents with an overall change; and
said plurality of data points acquired in step c serving to identify sample drift if a plot thereof presents with an overall change.
Said method then further comprises:
 e) if the first and second data points acquired from said first position on said sample in steps b and d are different, compensating said plurality of data points acquired from the second position in step c for the identified data acquisition system drift; and f) if the plurality of step e compensated second position step c acquired data points still present with an overall change, compensating said plurality of data points acquired in step c for the identified sample drift;

to the end that a sample characterizing data set which is compensated for sample and system drift during data acquisition is achieved.

In the foregoing Cases 1, 2 and 3 it is to be considered that the Time (T1) of application of an electromagnetic beam to a first location on a sample is far less than the time (T2) of application of an electromagnetic beam to a second location on a sample, (eg, a T2/T1>=about 10). In the following Case 4 it is to be understood that the times (T1) and (T2) are far less different from one another, (eg. T2/T1 is <=about 5 to 10, and optionally can even be equal to one another, or T1/T2 can be <=about 5 to 10).

CASE 4

In the case of the method of compensating a sample characterizing data set for sample and system drift during data acquisition, and where the times T1 and T2 of data acquisition at each of the first and second points respectively, is approximately the same or where one thereof is less than about 5-10 times the other, a method of determining sample and system drift comprises the steps of:

b) in an alternating fashion practicing steps b1 and b2, each a plurality of times, to provide two data sets:

b1) said first data set being obtained by causing a beam of electromagnetic radiation to impinge on a first position on said sample so that it interacts therewith and enters said detector, so that said detector provides as output, a data point set over a time T1, which is the total time electromagnetic radiation interacts with said first position;

b2) said second data set being obtained by causing said beam of electromagnetic radiation to impinge on a second position on said sample so that it interacts therewith and enters said detector, so that said detector provides a data point set over a time T2, which is the total time electromagnetic radiation interacts with said second position;

where T1 and T2 are about equal or one thereof is no more than about 5-10 times the other.

The method then involves:

c) observing that first order changes for the data sets obtained in step b are each comprised of two components:

DATA CHANGE1=SYSTEM DRIFT+SAMPLE DRIFT1; and

DATA CHANGE2=SYSTEM DRIFT+SAMPLE DRIFT2;

and determining at least one of:

$$\text{SAMPLE DRIFT2} = \frac{(\text{DATA CHANGE2} - \text{DATA CHANGE1})}{(1 - R12)};$$

or $$\text{SAMPLE DRIFT1} = \frac{(\text{DATA CHANGE1} - \text{DATA CHANGE2})}{(1 - R21)};$$

where $R12=T1/T2$ and $R21=T2/T1$. (Note if $T2>>T1$ or $T1>>T2$ then $R12$ or $R21=0.0$ and $(1-R12)$ and $(1-R21)$ are simply $(1.0)$).

From the foregoing the present invention method involves determining:

SYSTEM DRIFT=DATA CHANGE2-SAMPLE DRIFT2; and at least one of:

SAMPLE DRIFT2=DATA CHANGE2-SYSTEM DRIFT; and

SAMPLE DRIFT1=DATA CHANGE1-SYSTEM DRIFT;

such that values for sample drift1, sample drift2 and system drift terms are determined from empirically determined first order changes from said first and second data sets.

Said method can then, optionally, further comprises:

d) compensating at least one of the first and second data sets which correspond to the first and second positions on said sample for data acquisition system drift, sample drift or both; to the end that a sample characterizing data set which is compensated for sample and system drift during data acquisition is achieved.

In any of the cases the system provided in step a can further comprise a polarization state generator and a polarization state detector and the system to form an ellipsometer or polarimeter.

In the foregoing, as it is important, where data is acquired over a prolonged period of time at a point on a sample, energy deposited at that point can cause change of the sample, such as, for instance, by deposition of atmospheric components. Data acquired will reflect this influence as a "sample drift". While it is always difficult, where data acquisition times become more and more equal at two sample points, (eg. one time is less than 5 times the other), it becomes progressively more and more difficult to separately identify sample and system drift change components in an observed plot. However, data acquired at one of the points on the sample can be acquired during comparatively very short time periods. A basic assumption/premise of the present invention is that where acquisition time is comparatively short, data will not be significantly influenced by sample drift, but rather essentially only by system drift. Hence, where one sample point is investigated very quickly and another over a much longer, (eg. 10 times longer), time, it becomes possible to easily separately determine system and sample drift components.

It is also noted that when correcting a data set for drift an overall change can be used at each data point, or a change obtained in the region of a data point can be used for that point.

It is noted that in the above that Cases 1-4 are each a special case of a general scenario, based on values of R12.

For Cases 1 and 2, R12 is arbitrary, and:
For Case 1 Observed Data Change=Sample Drift; and
For Case 2 Observed Data Change=System Drift.
For Case 3 R12 or R21 can be small.
For Case 4 R12 or R21 is not small.

Further, for Cases 1-3, the change could be modeled by a non-linear equation, (eg. a polynomial or other mathematical equation). However, in Case 4 a linear equation is necessary as a result of the use of the ratio R12=T1/T2 or R21=T2/T1.

The disclosed present invention methodology can also include performing at least one selection from the group consisting of:

storing at least some data provided by said detector in machine readable media;

analyzing at least some of the data provided by said detector and storing at least some of the results of said analysis in machine readable media;

displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result; and analyzing at least some of the data provided by said detector and causing at least some thereof to produce a signal which is applied to provide a concrete and tangible result.

The present invention will be better understood by reference to the Detailed Description Section of this Specification, with reference to the Drawings.

DETAILED DESCRIPTION

Figure 1:
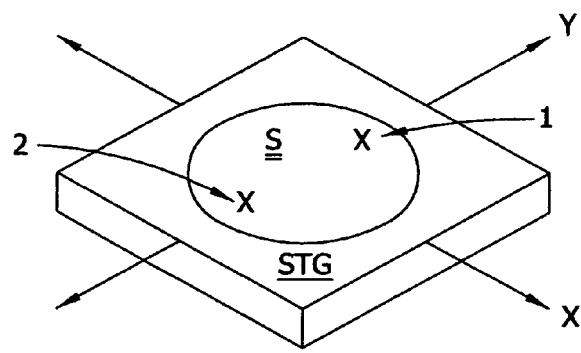
FIG. 1 shows a Sample (S) on a Stage (STG) which, it is indicated, a Means for Directing a Beam (B) of Electromagnetic Radiation from said Source (LS) thereof to impinge on a Sample (S) placed on said Stage (STG), and for controlling where upon said Sample (S) said Beam (B) impinges can be moved to position the Sample (S).

Turning now to the Drawings, FIG. 1 shows a Sample (S) on a Stage (STG) which, it is indicated, can be moved in demonstrative "X" and "Y directions to position the Sample (S) so that points (1) and (2) can be accessed. Other systems for accomplishing this, such as R-Theta stages, are to be considered equivalent.

Figure 2:
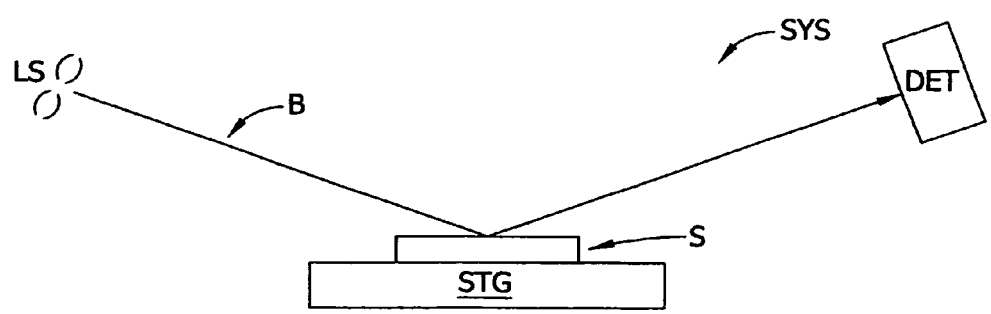
FIG. 2 shows a Data Acquisition System (SYS) for use in obtaining a Data Set.

FIG. 2 shows a Data Acquisition System (SYS) for use in obtaining a Data Set. The Data Acquisition System (SYS) comprises:

a Source (LS) of a beam (B) of electromagnetic radiation;
a Sample (S) Supporting Stage (STG);
a detector of electromagnetic radiation which exits said sample;

In view of the above, it is further noted that FIG. 1 indicates a Means for Controlling where a Beam (B) of Electromagnetic Radiation from said Source (LS) thereof impinges on a Sample (S) placed on said Stage (STG), (ie. for instance, Point "1" or Point "2"), via indication of "X" and "Y" movements. This could also be accomplished by an R-THETA stage or the like.

Figure 3:
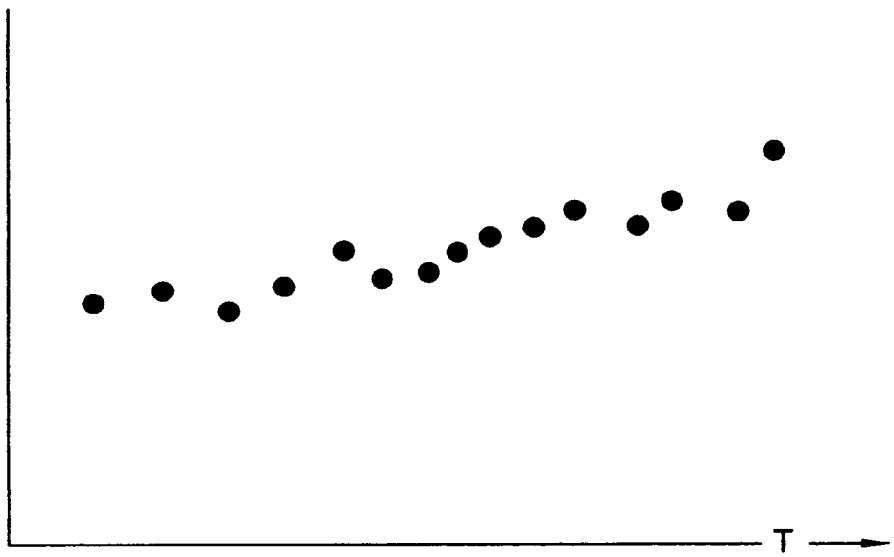
FIGS. 3 and 4 show plots of data indicating sample drift, and data corrected therefore, respectively, where system drift is negligible.
Figure 4:
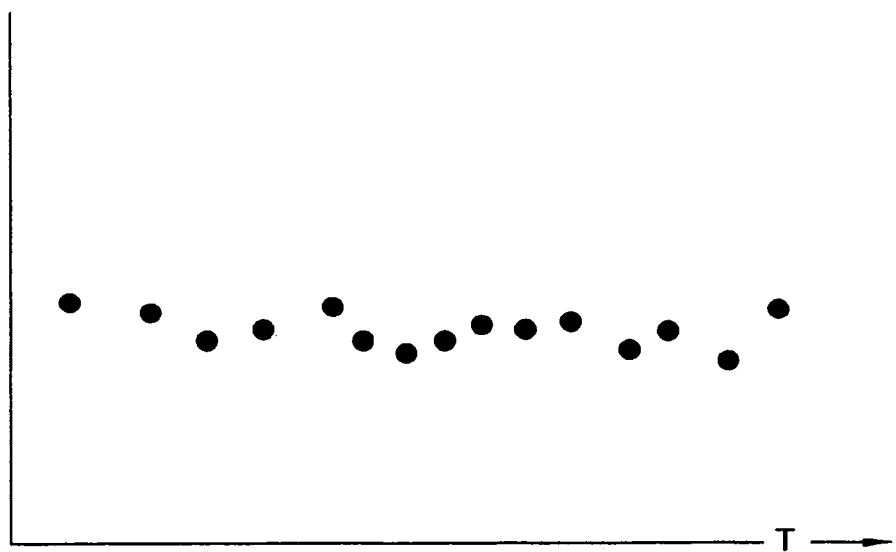
Figure 5:
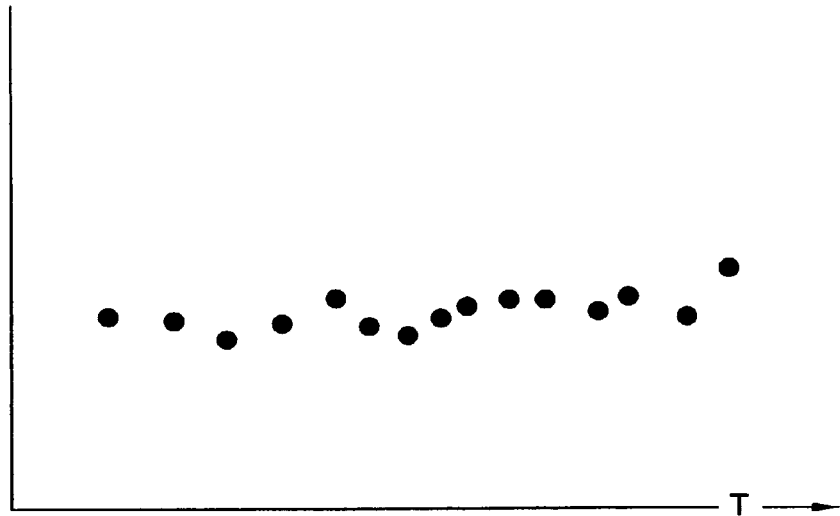
FIG. 5 shows data corrected for sample drift, but wherein system drift is not zero.

FIGS. 3 and 4 show very general introductory plots indicating sample drift, and data corrected for said sample drift, respectively, where system drift is negligible. The plots are best interpreted as demonstrative of data obtained from a single position on a sample over time. FIG. 5 shows, very generally, data which is corrected for sample drift, can still have imposed thereupon a change resulting from system drift which occurs during data acquisition and is not zero. FIGS. 8-14 which are described below, better disclose what FIGS. 2-5 generally disclose, in the specific context of the present invention methodology.

Figure 6:
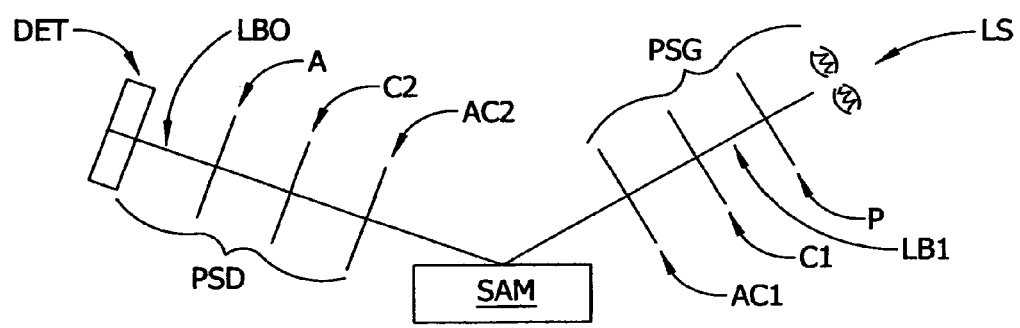
FIG. 6 shows the elements of an Ellipsometer or Polarimeter.

Continuing, as application of the present invention is particularly well suited for use in Ellipsometers and Polarimeters, FIG. 6 is included to show the basic elements of an Ellipsometer or Polarimeter. Note the presence of a Polarization State Generator (PSG) which serves to set a state of polarization in a Beam (B) of Electromagnetic Radiation provided by the Source (LS) thereof. Accompanying is a Polarization State Analyzer (PSA) for determining a change in polarization state caused by interaction with the Sample (SAM). When polarization state is not controlled by application of a (PSG), the system is a Reflectometer or Spectrophotometer. Also note the presence of Arms (SAI) and (SAO) which support the (LS) (PSG) and the (PSA) (DET) respectively. Also note the presence of a Guide (PRIG) for enabling movement of the Beam Directing Means (PRI) into and out of a Beam (B') before it enters the Data Detector (DET). This is a demonstrative, and not limiting, system for effecting the desired result.

Figure 7:
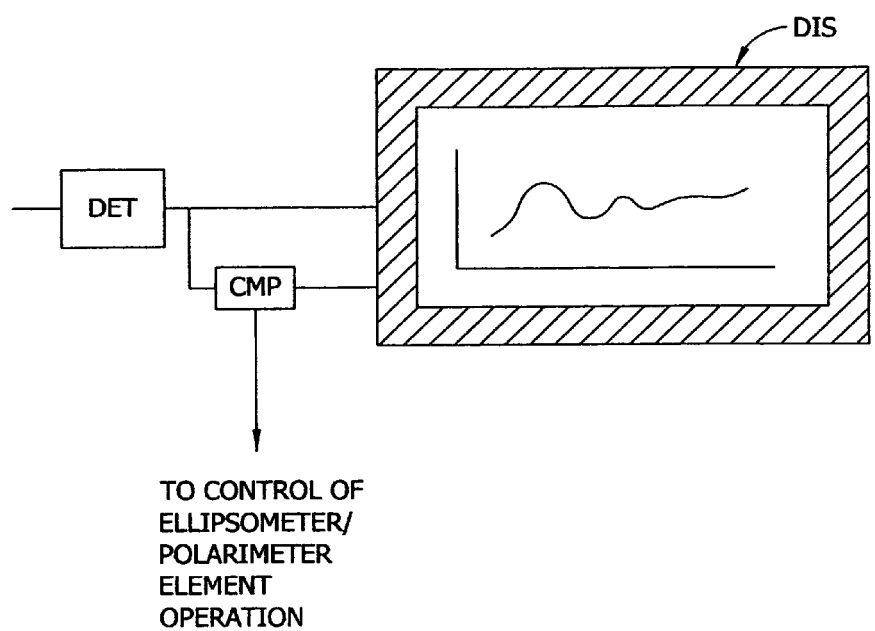
FIG. 7 is included to show that a present invention system can be controlled by a computer.

FIG. 7 is included to show that operation of a present invention system can be controlled by a Computer (CMP). Further, data provided by the Data Detector (DET), or analyzed results thereof, can be presented in a Display (DIS).

Figure 8:
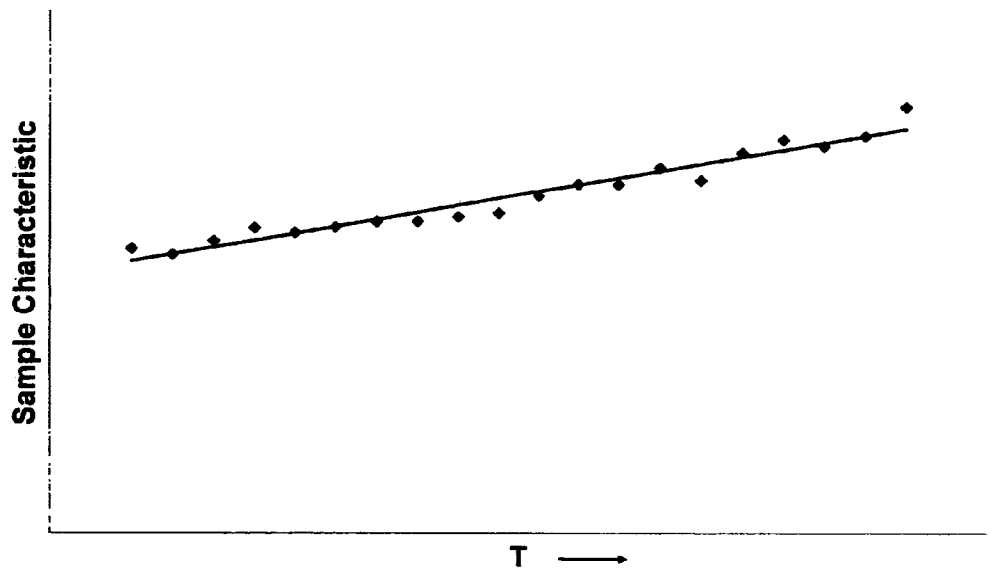
FIGS. 8 and 9 demonstrate a method of removing a first order change, (the solid line in FIG. 8), to remove the effects of sample drift and arrive at the results shown in FIG. 9.
Figure 9:
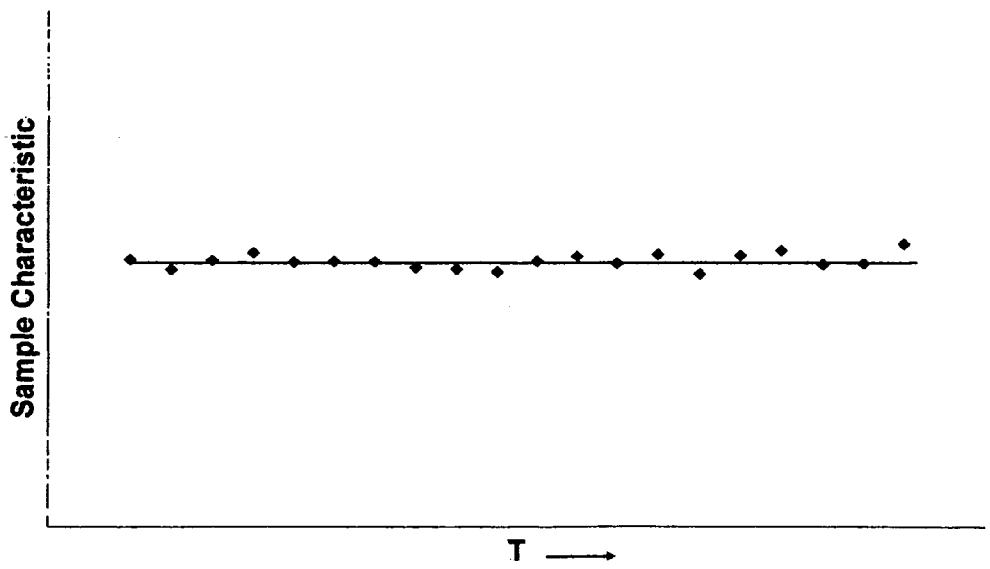

As indicated above, FIGS. 8 and 9 better demonstrate a method of removing a first order change, (the solid line in FIG. 8), to remove the effects of sample drift and arrive at the results shown in FIG. 9. Said FIGS. 8 and 9 demonstrate the results of practicing the methodology disclosed in the Disclosure of the Invention Section of this Specification which recite:

b) causing a beam of electromagnetic radiation to impinge on a position on said sample so that it interacts therewith and enters said detector, so that said detector provides as output, a plurality of data points over time;

said plurality of data points acquired in step b serving to identify sample drift if a plot thereof presents with an overall change;

said method further comprising:

c) if the plurality of data points acquired from the position in step b present with an overall change, compensating said plurality of data points acquired in step b for the identified sample drift;

to the end that a sample characterizing data set which is compensated for sample drift is achieved.

Figure 10:
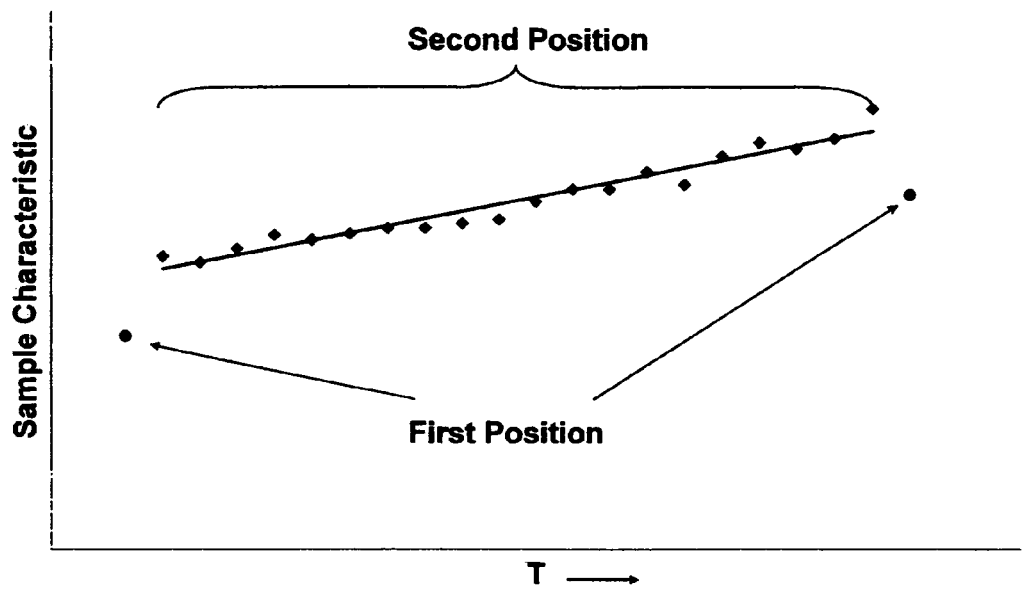
FIGS. 10 and 11 demonstrate a method of removing a first order change, (the solid line in FIG. 10), to remove the effects of system drift and arrive at the results shown in FIG. 11.
Figure 11:
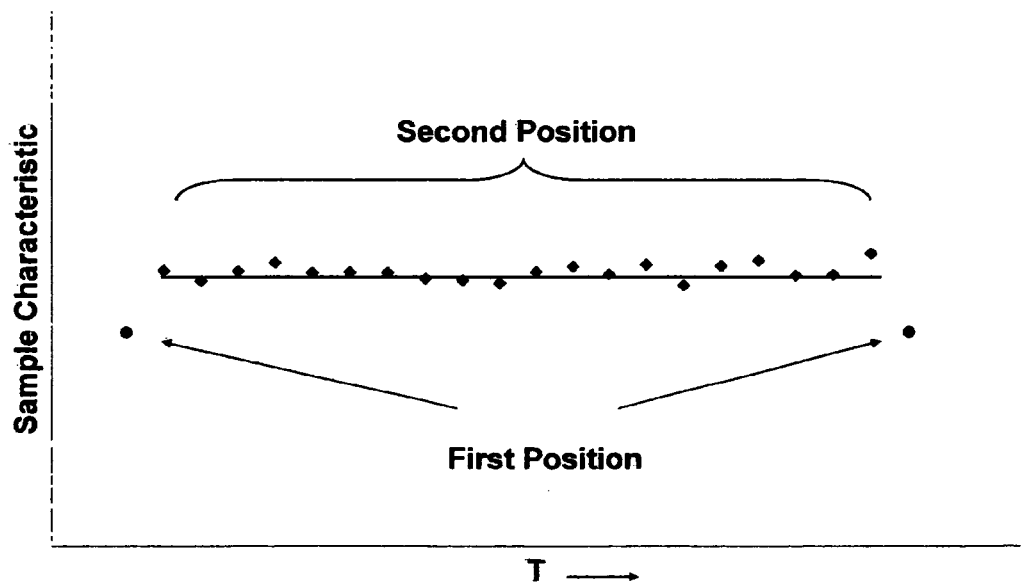

FIGS. 10 and 11 better demonstrate a method of removing a first order change, (the solid line in FIG. 10), to remove the effects of system drift and arrive at the results shown in FIG. 11. Said FIGS. 10 and 11 demonstrate the results of practicing the methodology disclosed in the Disclosure of the Invention Section of this Specification which recite:

b) causing a beam of electromagnetic radiation to impinge on a first position on said sample so that it interacts therewith and enters said detector, so that said detector provides as output, a first single data point in a brief period of time;

c) causing said beam of electromagnetic radiation to impinge on a second position on said sample so that it interacts therewith and enters said detector, so that said detector provides as output, a plurality of data points over time;

d) causing said beam of electromagnetic radiation to again impinge on said first position on said sample so that it interacts therewith and enters said detector, so that said detector provides as output, a second single data point in a brief period of time;

said first and second data points acquired from said first position on said sample in steps b and d serving to identify system drift during data acquisition if they are different and a plot thereof presents with an overall change; and said plurality of data points acquired in step c serving to identify sample drift if a plot thereof presents with an overall change;

said method further comprising:

e) if the first and second data points acquired from said first position on said sample in steps b and d are different, compensating said plurality of data points acquired from the second position in step c for the identify system drift during data acquisition;

to the end that a sample characterizing data set which is compensated for system drift during data acquisition is achieved.

Figure 12:
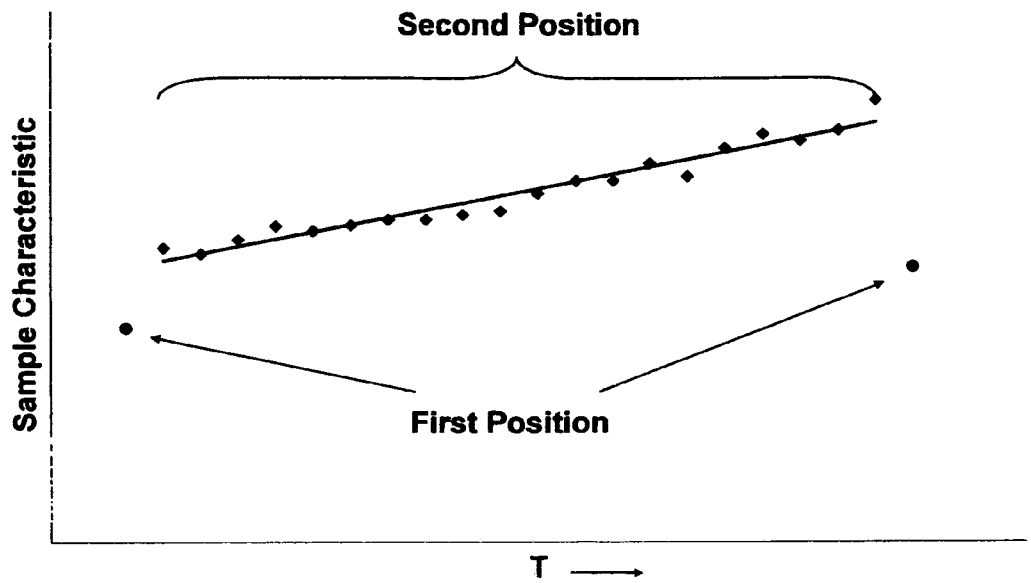
FIGS. 12, 13 and 14 demonstrate a method of removing first order changes, (the solid lines in FIGS. 12 and 13), to remove the effects of sample drift and system drift, and arrive at the results shown in FIG. 14.
Figure 13:
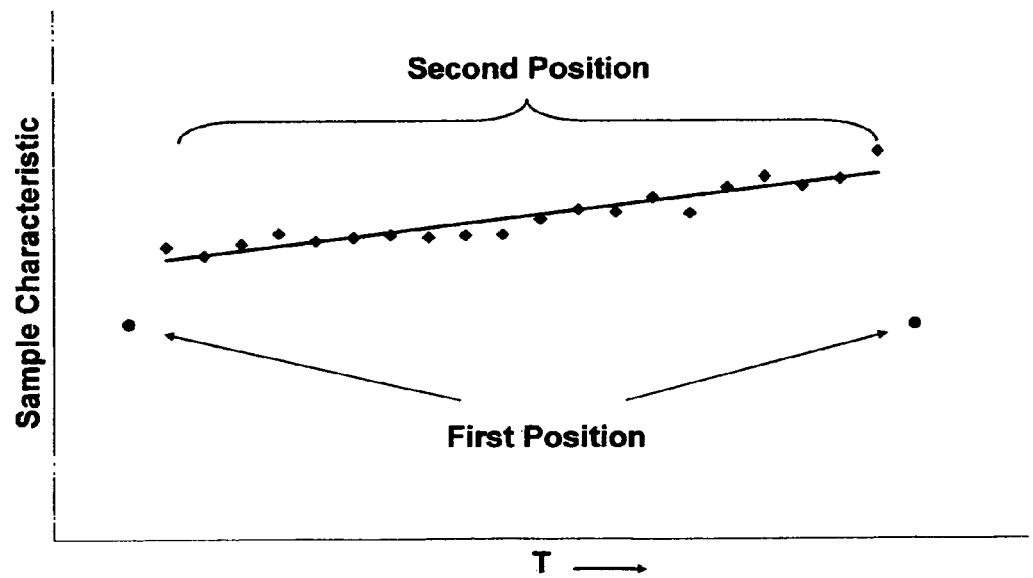
Figure 14:
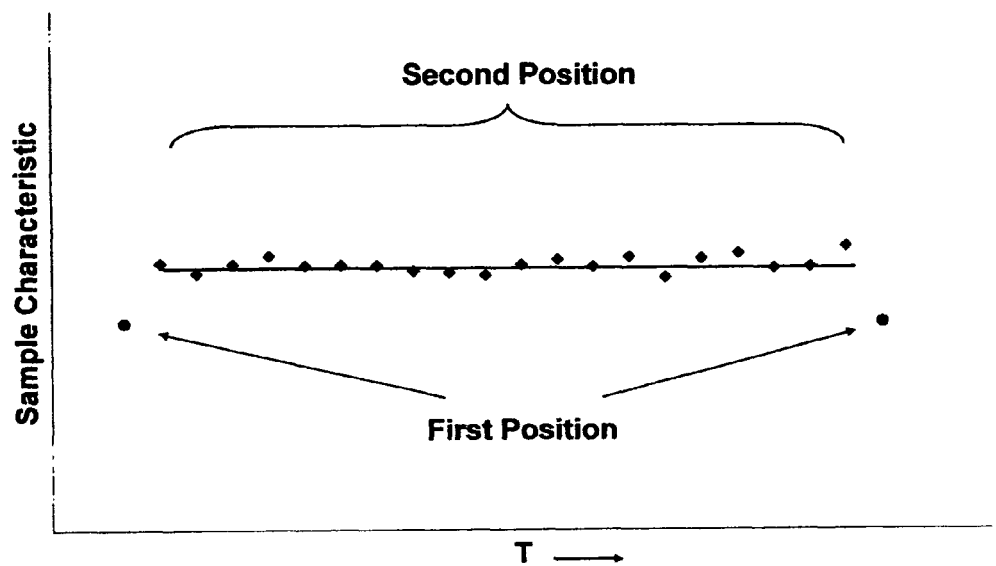

FIGS. 12, 13 and 14 better demonstrate a method of removing first order changes, (the solid lines in FIGS. 12 and 13), to remove the effects of sample drift and system drift, and arrive at the results shown in FIG. 14. Said FIGS. 12, 13 and 14 demonstrate the results of practicing the methodology disclosed in the Disclosure of the Invention Section of this Specification which recite:

b) causing a beam of electromagnetic radiation to impinge on a first position on said sample so that it interacts therewith and enters said detector, so that said detector provides as output, a first single data point in a brief period of time;

c) causing said beam of electromagnetic radiation to impinge on a second position on said sample so that it interacts therewith and enters said detector, so that said detector provides as output, a plurality of data points over time;

d) causing said beam of electromagnetic radiation to again impinge on said first position on said sample so that it interacts therewith and enters said detector, so that said detector provides as output, a second single data point in a brief period of time;

said first and second data points acquired from said first position on said sample in steps b and d serving to identify system drift during data acquisition if they are different and a plot thereof presents with an overall change; and said plurality of data points acquired in step c serving to identify sample drift if a plot thereof presents with an overall change;

said method further comprising:

e) if the first and second data points acquired from said first position on said sample in steps b and d are different, compensating said plurality of data points acquired from the second position in step c for the identify data acquisition system drift; and f) if the plurality of step e compensated second position step c acquired data points still present with an overall change, compensating said plurality of data points acquired in step c for the identified sample drift;

to the end that a sample characterizing data set which is compensated for sample and system drift during data acquisition is achieved.

Figure 15:
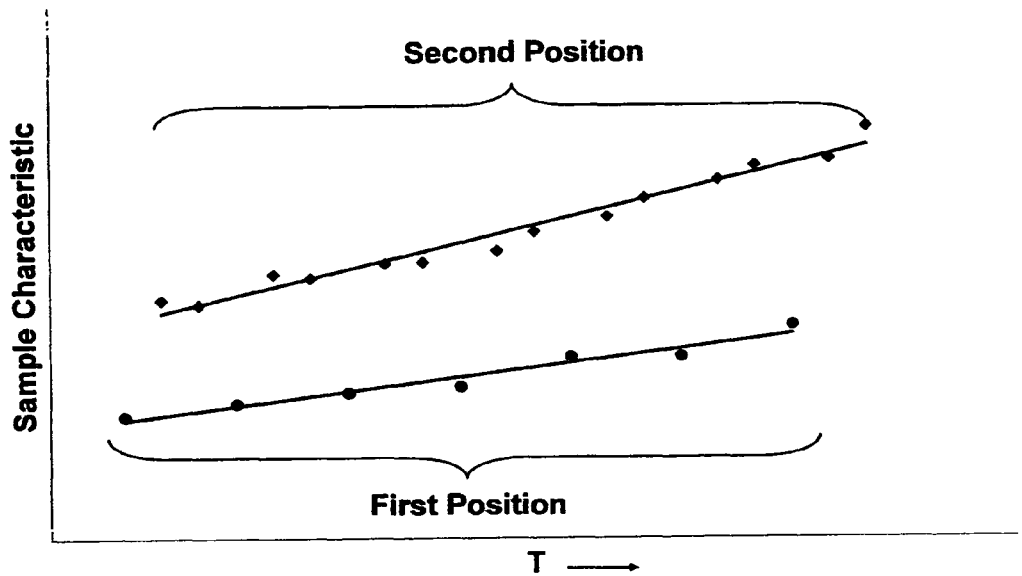
FIGS. 15 and 16 demonstrate a method of removing first order change, (the solid lines in FIG. 15), to identify the effects of system drift and sample drift where two points on a sample are investigated using similar data acquisition times, and arrive at the results shown in FIG. 16.
Figure 16:
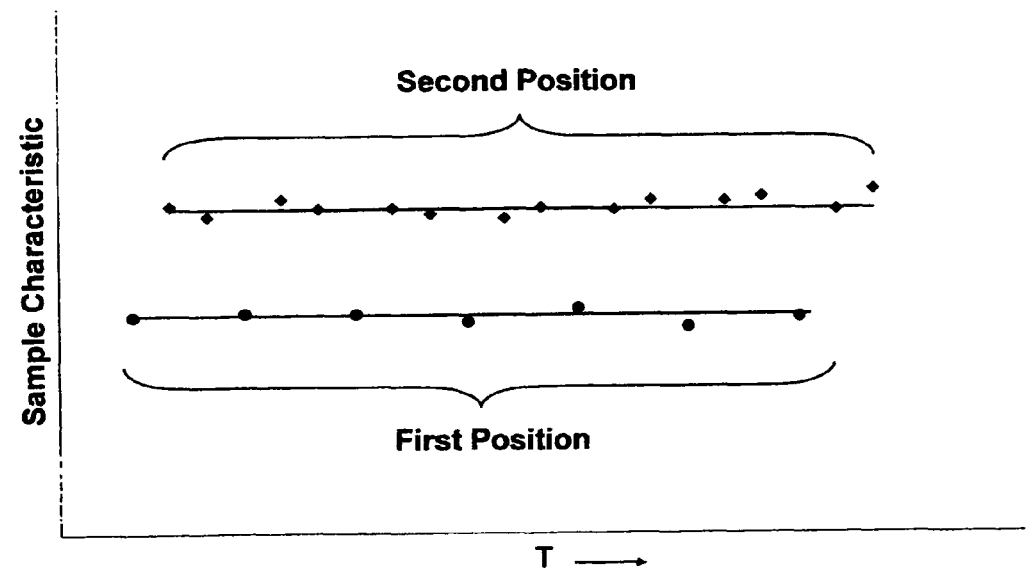

In addition, FIGS. 15 and 16 demonstrate a method of identifying a first order change, (the solid lines in FIG. 15 which is shown for the case of R12 being equal to about 0.5), to identify the effects of system drift and sample drift where two points on a sample are investigated using similar data acquisition times, and arrive at the results shown in FIG. 16. Said FIGS. 15 and 16 demonstrate the results of practicing the methodology disclosed in the Disclosure of the Invention Section of this Specification which recite:

b) in an alternating fashion practicing steps b1 and b2, each a plurality of times, to provide two data sets:

b1) said first data set being obtained by causing a beam of electromagnetic radiation to impinge on a first position on said sample so that it interacts therewith and enters said detector, so that said detector provides as output, a data point set over a time T1, which is the total time electromagnetic radiation interacts with said first position;

b2) said second data set being obtained by causing said beam of electromagnetic radiation to impinge on a second position on said sample so that it interacts therewith and enters said detector, so that said detector provides a data point set over a time T2, which is the total time electromagnetic radiation interacts with said second position;

where T1 and T2 are about equal or one thereof is no more than about five times the other.

The method then involves:

c) observing that first order changes for the data sets obtained in step b are each comprised of two components:

DATA CHANGE1=SYSTEM DRIFT+SAMPLE DRIFT1; and

DATA CHANGE2=SYSTEM DRIFT+SAMPLE DRIFT2;

and determining at least one of:

$$\text{SAMPLE DRIFT2} = \frac{(\text{DATA CHANGE2} - \text{DATA CHANGE1})}{(1 - R12)};$$

or $$\text{SAMPLE DRIFT1} = \frac{(\text{DATA CHANGE1} - \text{DATA CHANGE2})}{(1 - R21)};$$

where R12=T1/T2 and R21=T2/T1;

said method further involving determining:

SYSTEM DRIFT=DATA CHANGE2−SAMPLE DRIFT2; and at least one of:

SAMPLE DRIFT2=DATA CHANGE2−SYSTEM DRIFT; and

SAMPLE DRIFT1=DATA CHANGE1−SYSTEM DRIFT;

such that values for SAMPLE DRIFT1, SAMPLE DRIFT2 and SYSTEM DRIFT terms are determined from empirically determined first order changes from said first and second data sets. Optional additional steps can then involve use of the so determined sample drifts and system drift to correct data.

It is noted that "Sample Characteristics" in FIGS. 8-16 can be any relevant measurable sample characterizing quantity, such as Intensity, Ellipsometric PSI or Ellipsometric DELTA or the like, as well as quantities derived therefrom, (eg. sample thin film thickness). Also, points (1) and (2) in FIG. 1 correspond to data presented as (First Position) and (Second Position), in FIGS. 8-16.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of compensating a sample characterizing data set for sample and system drift during data acquisition, comprising the steps of:
   a) providing a system comprising:
      a source of a beam of electromagnetic radiation;
      a sample supporting stage;
      means for controlling where a beam of electromagnetic radiation from said source impinges on a sample placed on said stage; and
      a detector of electromagnetic radiation which exits said sample;
   b) in an alternating fashion practicing steps b1 and b2, each a plurality of times, to provide two data sets:
      b1) a first data set being obtained by causing a beam of electromagnetic radiation to impinge on a first position on said sample so that it interacts therewith and enters said detector, so that said detector provides as output, a data point set over a time T1, which is the total time electromagnetic radiation interacts with said first position;
      b2) a second data set being obtained by causing said beam of electromagnetic radiation to impinge on a second position on said sample so that it interacts therewith and enters said detector, so that said detector provides a data point set over a time T2, which is the total time electromagnetic radiation interacts with said second position;
   c) defining first order changes for the data sets obtained in step b as:

DATA CHANGE1=SYSTEM DRIFT+SAMPLE DRIFT1; and

DATA CHANGE2=SYSTEM DRIFT+SAMPLE DRIFT2;

and therefrom determining:

$$\text{SAMPLE DRIFT2} = \frac{(\text{DATA CHANGE2} - \text{DATA CHANGE1})}{(1 - R12)};$$

where R12=T1/T2;
and:

SYSTEM DRIFT=DATA CHANGE2−SAMPLE DRIFT2; and

SAMPLE DRIFT1=DATA CHANGE1−SYSTEM DRIFT;

such that values for sample drift1, sample drift2 and system drift terms are determined from first order changes from said first and second data sets;
said method further, optionally, comprising:
   d) compensating at least one of the first and second data sets which correspond to the first and second positions on said sample for data acquisition system drift, sample drift or both;
to the end that a sample characterizing data set which is compensated for sample and system drift during data acquisition is achieved.

2. A method as in claim 1, in which the system provided in step a further comprises a polarization state generator and a polarization state detector and the system is an ellipsometer or polarimeter.

3. A method as in claim 1 which further comprises at least one selection form the group consisting of:
   storing at least some data provided by said detector in machine readable media;
   analyzing at least some of the data provided by said detector and storing at least some of the results of said analysis in machine readable media;
   displaying at least some data provided by said detector by electronic and/or non-electronic means;
   analyzing at least some of the data provided by said detector and displaying at least some of the results of said analysis by electronic and/or non-electronic means;
   causing at least some data provided by said detector to produce a signal which is applied to provide a concrete and tangible result; and
   analyzing at least some of the data provided by said detector and causing at least some thereof to produce a signal which is applied to provide a concrete and tangible result.

4. A method as in claim 1, in which, prior to step c, T1 and T2 are characterized by a selection from the group consisting of:
   they are substantially equal; and
   one thereof is no more than about 5-10 times the other.

5. A method of compensating a sample characterizing data set for sample and system drift during data acquisition, comprising the steps of:
   a) providing a system comprising:
      a source of a beam of electromagnetic radiation;
      a sample supporting stage;
      means for controlling where a beam of electromagnetic radiation from said source impinges on a sample placed on said stage; and
      a detector of electromagnetic radiation which exits said sample;
   b) in an alternating fashion practicing steps b1 and b2, each a plurality of times, to provide two data sets:
      b1) a first data set being obtained by causing a beam of electromagnetic radiation to impinge on a first position on said sample so that it interacts therewith and enters said detector, so that said detector provides as output, a data point set over a time T1, which is the total time electromagnetic radiation interacts with said first position;
      b2) a second data set being obtained by causing said beam of electromagnetic radiation to impinge on a second position on said sample so that it interacts therewith and enters said detector, so that said detector provides a data point set over a time T2, which is the total time electromagnetic radiation interacts with said second position;

c) defining first order changes for the data sets obtained in step b as:

$$\text{DATA CHANGE1} = \text{SYSTEM DRIFT} + \text{SAMPLE DRIFT1;  and}$$

$$\text{DATA CHANGE2} = \text{SYSTEM DRIFT} + \text{SAMPLE DRIFT2;}$$

and therefrom determining:

$$\text{SAMPLE DRIFT2} = \frac{(\text{DATA CHANGE2} - \text{DATA CHANGE1})}{(1 - R12)};$$

and/or $$\text{SAMPLE DRIFT1} = \frac{(\text{DATA CHANGE1} - \text{DATA CHANGE2})}{(1 - R21)};$$

where R12=T1/T2 and R21=T2/T1;

said method further involving determining:

$$\text{SYSTEM DRIFT} = \text{DATA CHANGE1} - \text{SAMPLE DRIFT1;}$$

$$\text{SAMPLE DRIFT2} = \text{DATA CHANGE2} - \text{SYSTEM DRIFT; and}$$

such that values for sample drift1, sample drift2 and system drift terms are determined from first order changes from said first and second data sets;

said method further, optionally, comprising:

d) compensating at least one of the first and second data sets which correspond to the first and second positions on said sample for data acquisition system drift, sample drift or both;

to the end that a sample characterizing data set which is compensated for sample and system drift during data acquisition is achieved.

6. A method as in claim 5, in which the system provided in step a further comprises a polarization state generator and a polarization state detector and the system is an ellipsometer or polarimeter.

7. A method as in claim 5 which further comprises at least one selection form the group consisting of:

storing at least some data provided by said detector in machine readable media;

analyzing at least some of the data provided by said detector and storing at least some of the results of said analysis in machine readable media;

displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result; and analyzing at least some of the data provided by said detector and causing at least some thereof to produce a signal which is applied to provide a concrete and tangible result.

8. A method as in claim 5, in which, prior to step c, T1 and T2 are characterized by a selection from the group consisting of:

they are substantially equal; and one thereof is no more than about 5-10 times the other.

* * * * *